US00PP17087P3

(12) United States Plant Patent

Ishihara et al.

(10) Patent No.: US PP17,087 P3

(45) Date of Patent: Sep. 12, 2006

(54) *PETUNIA* PLANT NAMED 'SUNCOPAPIN'

(50) Latin Name: *Petunia hybrida*
Varietal Denomination: Suncopapin

(75) Inventors: Takuro Ishihara, Higashikurume (JP); Kazunari Iwaki, Omihachiman (JP); Kiyoshi Miyazaki, Hikone (JP); Shinya Miyano, Katori-gun (JP)

(73) Assignees: Suntory Flowers Limited, Tokyo (JP); Keisei Rose Nurseries, Inc., Tokyo (JP)

( * ) Notice: Subject to any disclaimer, the term of this patent is extended or adjusted under 35 U.S.C. 154(b) by 323 days.

(21) Appl. No.: 10/812,865

(22) Filed: Mar. 29, 2004

(65) Prior Publication Data

US 2005/0217002 P1 Sep. 29, 2005

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

| | | | | |
|---|---|---|---|---|
| PP6,899 | P | 7/1989 | Tsuda et al. | |
| PP6,914 | P | 7/1989 | Tsuda et al. | |
| PP6,915 | P | 7/1989 | Tsuda et al. | |
| PP9,322 | P | 10/1995 | Tachibana et al. | |
| PP9,556 | P | 5/1996 | Tachibana et al. | |
| 2003/0131391 | P1 * | 7/2003 | Miyazaki et al. | Plt./356 |

FOREIGN PATENT DOCUMENTS

| | | |
|---|---|---|
| JP | PBR 4010 | 3/1994 |
| JP | PBR 11137 | 3/2003 |

OTHER PUBLICATIONS

Germania Seed Homepage http://www.germaniaseed.com.*
http://www.germaniaseed.com/pdf/04–747Pineae.pdf Suntory Collection and Other Specialty Annuals.*
UPOV ROM GTITM Computer Database, GTI Jouve Retrieval Software 2004/06 Citation for 'Suncopapin.*
Flower & Green Catalog 2001, Suntory Flowers, Ltd., (3 pp), Published 2000, with brief English explanation and partial translation of p. 7.
The 2004 Suntory Collection, Jackson & Perkins Wholesale, Inc., (3 pp), Published 2002, with brief English translation of last page.
Pineae Peak Performers featuring the 2004 Suntory Collection, Pineae Greenhoses, Inc., (4 pp), Published 2003 with brief English translation of the 3rd and last page.
Suntory Collection 2001, Moerheim New Plant bv, (3 pp), Published 2000 with brief English translation of last page.
Suntory Collection 2004, Moerheim New Plant bv, (3 pp), Published 2003 with brief English translation of last page.
Colour Wave Collection 2003–04, Ramm Botanicals Pty Ltd., (3 pp), Published 2002 with brief English translation of last page.
Explanation of Publications of Japanese PBR Registrations and family documents therein.

* cited by examiner

*Primary Examiner*—Howard J. Locker
*Assistant Examiner*—W. C. Haas
(74) *Attorney, Agent, or Firm*—Christie, Parker & Hale, LLP

(57) ABSTRACT

Disclosed herein is a new and distinct variety of *Petunia* plant having a decumbent habit and short stems. The *Petunia* plant has abundant branching, and a great profusion of blooms, the whole plant remaining in bloom for a considerable period of time. The flowers are single and small, the petals having vivid reddish purple color. The inside color of the corolla throat is light purplish pink and the outside of the corolla tube is pale yellow green. The plant exhibits high resistance to heat, cold and disease.

2 Drawing Sheets

Botanical designation: *Petunia hybrida.*
Variety denomination: 'Suncopapin'.

BACKGROUND OF THE VARIETY

The present invention relates to a new and distinct variety of *Petunia* plant originated from crossing of a *Petunia* hybrid variety called '9Pt-13a' as the female parent and '96PWE-5-C20' as the male parent.

The *Petunia* is a very popular plant that is used for flower bedding and potting in the summer season. There are only a few *Petunia* varieties known to the inventors which do not have an upright growth habit and which have a high resistance to rain, heat, and disease. *Petunias* of the Revolution series include 'Revolution Purple pink' (U.S. Plant Pat. No. 6,915), 'Revolution Brilliant pink' (U.S. Plant Pat. No. 6,914), 'Revolution Brilliantpink-Mini' (U.S. Plant Pat. No. 6,899), and 'Revolution Blue vein' (U.S. Plant Pat. No. 9,322). These are decumbent type plants having long stems, a low plant height, abundant branching, and a high resistance to heat, rain and disease. However, there are only a few *Petunia* varieties known to the inventors having a decumbent and compact plant shape, a great profusion of small size flowers, reddish purple petals and a high resistance to rain, heat, and disease. Accordingly, this invention was aimed at obtaining a new *Petunia* variety having vivid reddish purple petals, together with the above features.

Progress

The female parent '9Pt-13a' (unpatented) used in the crossing of 'Suncopapin' is a strain of our breeding lines, having a spreading growth habit with many branches. It has medium size single flowers, the petals having vivid reddish purple color. The growth of the female parent, '9Pt-13a' is spreading, while that of 'Suncopapin' is decumbent.

The male parent '96PWE-5-C20' (unpatented) used in the crossing of 'Suncopapin' is a strain of our breeding lines, having a decumbent growth habit with many branches. It has small single flowers, the petals having a yellowish white color with pale purplish pink eye. The size of the flower of the male parent '96PWE-5-C20' is smaller than that of 'Suncopapin'.

In July 2000, crossing of '9Pt-13a' as the female parent and '96PWE-5-C20' as the pollen parent was conducted at Yokaichi-shi, Shiga-ken, Japan. In April 2001, 80 seedlings were obtained from that crossing. These seedlings were grown in pots in glasshouses and were evaluated. One seedling was selected in view of its growth habit, flower size and color in September 2001. That seedling was propagated by cutting and a trial was carried out by flower potting and bedding from April to September 2002 at Yokaichi-shi, Shiga-ken, Japan. The botanical characteristics of that plant were then examined, using similar varieties 'Sunmipi' (unpatented) and 'Revolution Pinkmini' (U.S. Plant Pat. No. 9,556) for comparison. As a result, it was concluded that this *Petunia* plant is distinguishable from any other variety, whose existence is known to us, and is uniform and stable in its characteristics. Then the new variety of *Petunia* plant was named 'Suncopapin'.

In the following description, the color-coding is in accordance with The R.H.S. Colour Chart.

SUMMARY OF THE VARIETY

This new variety is unlike any *Petunia* commercially available, known to the inventors, as evidenced by the following unique combinations of characteristics.

1. Rather compact and decumbent growth habit with short stems.
2. Having abundant branching and a great profusion of blooms.
3. The flowers are single and small. The petal color is vivid reddish purple (R.H.S.74A).
4. The plant has a high resistance to cold, heat and disease.

The new variety 'Suncopapin' differs from the similar variety 'Sunmipi' (unpatented) in the following points.

1. The spreading area of 'Suncopapin' is smaller than that of 'Sunmipi'.
2. The stem of 'Suncopapin' is shorter and thinner than that of 'Sunmipi'.
3. The internode length of 'Suncopapin' is shorter than that of 'Sunmipi'.
4. The leaf of 'Suncopapin' is shorter and thinner than that of 'Sunmipi'.
5. The bottom color of corolla throat 'Suncopapin' is light purplish pink (R.H.S. 65B) and the outside color of corolla throat is pale yellow green (R.H.S.145D). That of 'Sunmipi' is purplish white (R.H.S. N155B) and strong purplish pink (R.H.S. 73B).
6. The apex shape of petal of Suncopapin is obtuse. That of 'Sunmipi' is rounded.

The new variety 'Suncopapin' differs from the similar variety 'Revolution Pinkmini' (U.S. Plant Pat. No. 9,556) in the following points.

1. The spreading area of 'Suncopapin' is smaller than that of 'Revolution Pinkmini'.
2. The stem of 'Suncopapin' is thinner than that of 'Revolution Pinkmini'.
3. The leaf of 'Suncopapin' is shorter and thinner than that of 'Revolution Pinkmini'.
4. The petal color of 'Suncopapin' is vivid reddish purple (R.H.S.74A). That of 'Revolution Pinkmini' is deep purplish pink (R.H.S.68A).
5. The apex shape of petal of 'Suncopapin' is obtuse. That of 'Revolution Pinkmini' is rounded.

The new variety of *Petunia* plant 'Suncopapin' was asexually reproduced by the use of cuttings at Yokaichi-shi, Shiga-ken, Japan, and the homogeneity and stability thereof were confirmed. The instant plant retains its distinctive characteristics and reproduces true to type in successive generations.

BRIEF DESCRIPTION OF THE PHOTOGRAPH

The depicted plants had been reproduced by the use of cuttings and were photographed during July 2003 while growing outdoors in 15 cm pots at an age of approximately 6 months at Yokaichi-shi, Shiga, Japan.

DESCRIPTION OF VARIETY

Figure 1:
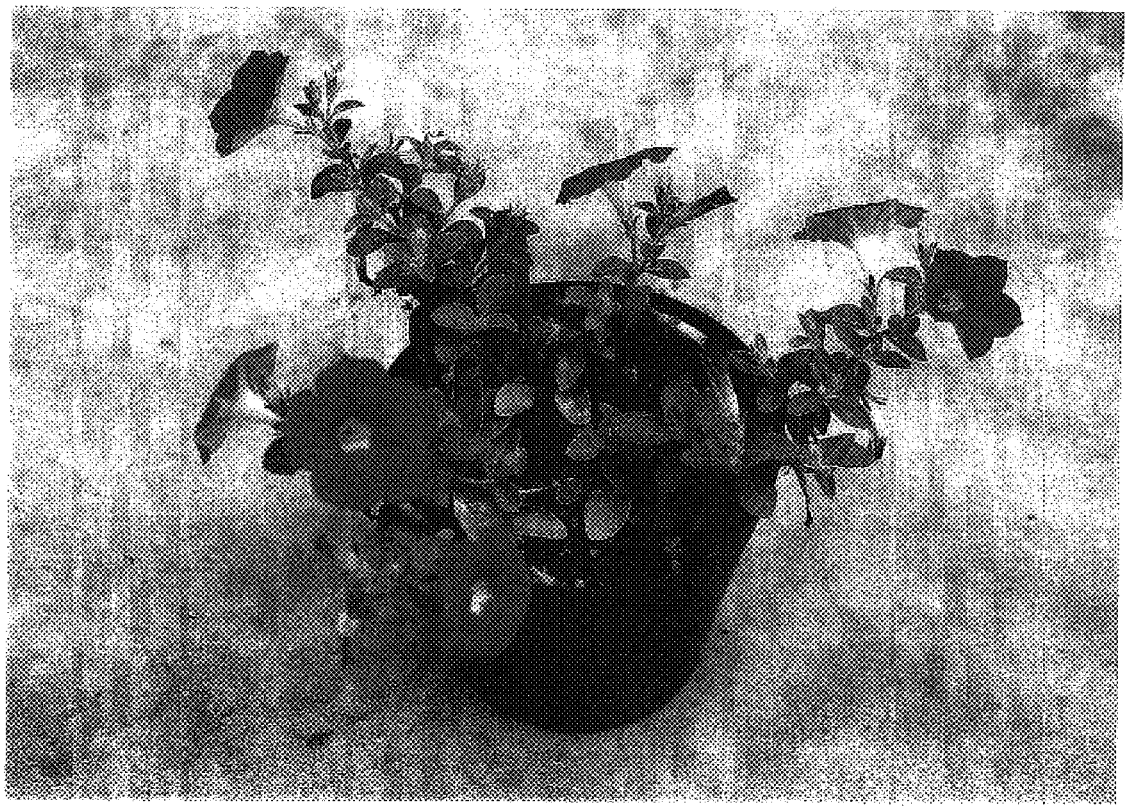
FIG. 1 illustrates a typical plant of the new variety of *Petunia* plant 'Suncopapin' while growing in a pot.
Figure 2:
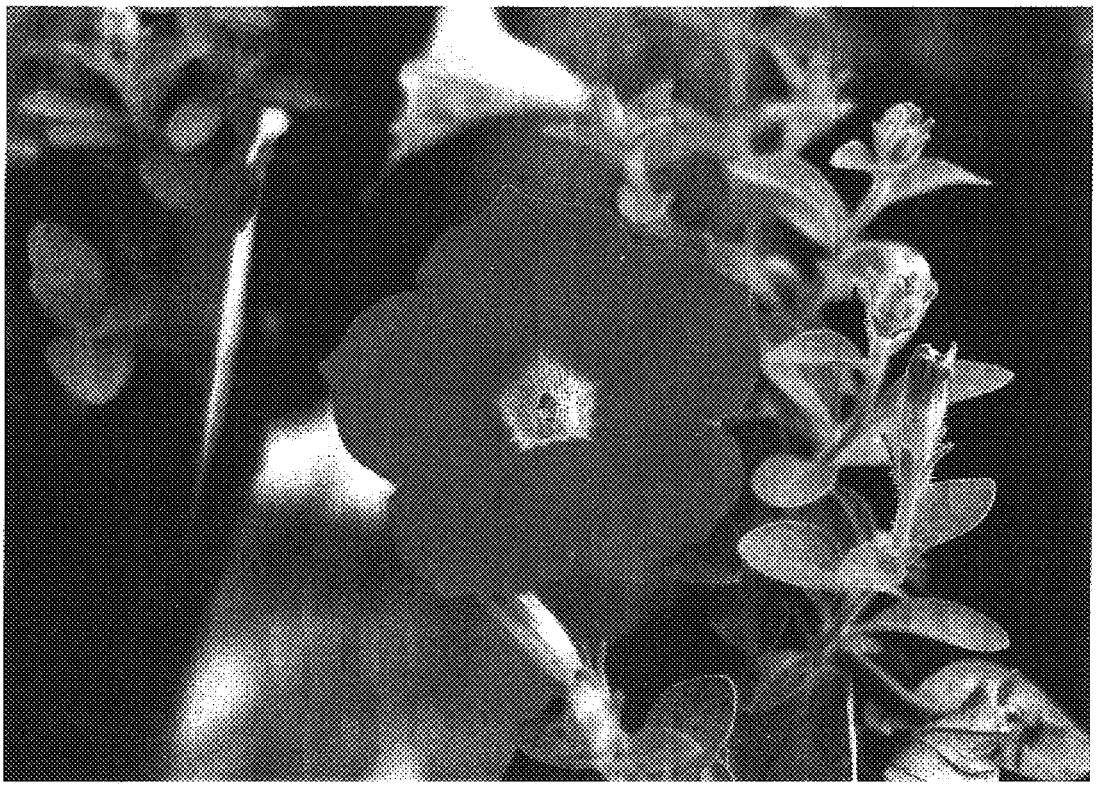
FIG. 2 illustrates a close view of typical foliage and a blossom of the new variety of *Petunia* plant 'Suncopapin'.

The botanical characteristics of the new and distinct variety of *Petunia* plant named 'Suncopapin' are as follows when observed as grown in typical outdoor conditions during July at Yokaichi-shi, Shiga-ken, Japan at an age of approximately 6 months. The average day temperature is approximately 22° C. and the average night temperature is approximately 12° C.

Plant:

*Growth habit.*—Decumbent.
*Plant height.*—Approximately 14.0 cm.
*Spreading area of plant.*—Approximately 23.8 cm.
*Blooming period.*—Early April to late October in the southern Kanto area, Japan. The plant shape does not change throughout this period. A typical flower commonly lasts approximately 5 days on the plant when experiencing a temperature of approximately 20° C.

Stem:

*Length.*—Approximately 2.5 cm.
*Diameter.*—Approximately 1.7 mm.
*Pubescence.*—Present and typical of the species.
*Branching.*—Approximately 4.
*Internode length.*—Approximately 1.3 cm.
*Color.*—R.H.S. 146B (moderate yellow green).

Leaf:

*Whole shape.*—Elliptic with entire margin. The apex shape is acute, and the base shape is attenuate.
*Length.*—Approximately 3.3 cm.
*Width.*—Approximately 2.2 cm.
*Color.*—Upper side color is R.H.S. 146A (moderate olive green). Lower side color is R.H.S. 144A (strong yellow green).
*Thickness.*—Approximately 0.2 mm.
*Pubescence.*—Sparse.

Flower:

*Facing direction.*—Slanted upward.
*Type.*—Single.
*Shape.*—Funnel-shaped, with five-fissures.
*Shape of petal tip.*—Obtuse.
*Lobation.*—Shallow.
*Waving of petal.*—Weak.
*Diameter.*—Approximately 4.4 cm.
*Depth.*—Approximately 2.8 cm.
*Upper petal surface color.*—Near R.H.S. 74A.
*Lower petal surface color.*—Near R.H.S. 75C.
*Inside color of flower throat.*—R.H.S. 65B.
*Outside color of flower tube.*—R.H.S. 145D.

Calyx:

*Diameter.*—Approximately 15 mm.
*Depth.*—Approximately 10 mm.
*Color* (*upper and lower surfaces*).—Near R.H.S. 147B.
*Texture* (*both surfaces*).—Smooth.
*Reproductive organs.*—1 normal pistil and 5 normal stamens. Color of pistil is R.H.S. 154C (light yellow green). Color of stamen is R.H.S. 144D (light yellow green).

Peduncle:

*Diameter.*—Approximately 0.9 mm.
*Length.*—Approximately 1.4 cm.
*Color.*—Near R.H.S. 146B.
*Texture.*—Smooth.
*Calyx.*—Narrow. 5 sepals in fused at the base.
*Physiological and ecological characteristics.*—High resistance to cold, heat and disease. Moderate resistance to rain and pests. 'Suncopapin' has a low temperature tolerance of at least 5° C.

Seed production has not been observed.

This new variety of *Petunia* plant is most suitable for flower bedding and potting, particularly in hanging pots or planters. Pinching of old blossoms will enhance the formation of new blossoms.

It is claimed:

1. A new and distinct variety of *Petunia* plant named 'Suncopapin', substantially as herein illustrated and described.

* * * * *